United States Patent [19]

Py

[11] Patent Number: 5,267,986
[45] Date of Patent: Dec. 7, 1993

[54] CARTRIDGE FOR APPLYING MEDICAMENT TO AN EYE FROM A DISPENSER

[75] Inventor: Daniel Py, Short Hills, N.J.

[73] Assignee: Self-Instill & Co., Inc., Natick, Mass.

[21] Appl. No.: 863,943

[22] Filed: Apr. 6, 1992

[51] Int. Cl.⁵ ............................................. A61M 35/00
[52] U.S. Cl. .................................... 604/294; 604/295; 222/214; 222/336
[58] Field of Search ............... 604/294, 295, 300, 302; 222/183, 214, 336, 420

[56] References Cited

U.S. PATENT DOCUMENTS

| | | | |
|---|---|---|---|
| 3,563,415 | 2/1971 | Ogle | 222/420 |
| 3,741,439 | 6/1973 | Vehrs | 222/214 |
| 3,993,064 | 11/1976 | McCarthy et al. | 604/294 |
| 4,471,890 | 9/1984 | Dougherty | 604/302 |
| 4,634,023 | 1/1987 | Tanaka et al. | 222/214 |
| 4,784,652 | 11/1988 | Wikström | 604/294 |
| 4,792,334 | 12/1988 | Py | 604/295 |
| 4,946,452 | 8/1990 | Py | 604/301 |
| 4,981,479 | 1/1991 | Py | 604/300 |
| 4,982,875 | 1/1991 | Pozzi et al. | 222/420 |
| 5,024,355 | 6/1991 | Jouillat et al. | 222/162 |
| 5,133,702 | 7/1992 | Py | 604/300 |
| 5,154,702 | 10/1992 | Foyil | 222/420 |
| 5,163,583 | 11/1992 | Whitworth | 222/420 |

*Primary Examiner*—Randall L. Green
*Assistant Examiner*—Gina M. Gualtieri
*Attorney, Agent, or Firm*—Kenyon & Kenyon

[57] ABSTRACT

A cartridge for actuating a piston-like or accordion-like dispenser-vial for applying medicament to an eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a trigger mechanism for releasing the cylinder from the locked position so that a drop is released from the dispenser. The housing includes a finger for engaging the lower eyelid and exposing the conjunctival cul de sac.

8 Claims, 3 Drawing Sheets

CARTRIDGE FOR APPLYING MEDICAMENT TO AN EYE FROM A DISPENSER

BACKGROUND OF THE INVENTION

1. Field of the Invention

The invention relates to a cartridge for applying medicament to an eye from a vial-dispenser of the type which is actuated by compression of the vial between its nozzle and its bottom wall.

2. Description of Related Art

There are various dispensers which are known for applying medicament to an eye. A typical eye-drop container includes a flexible vial storage portion and a nozzle for dispensing drops of medicament into the eye by squeezing the vial between its side walls. Less common, but more precise, are accordion-like or piston-like dispensers which are actuated by squeezing the vial between a bottom wall and the nozzle so as to compress the vial in its longitudinal direction, rather than from its sides. It is these accordion-like or piston-like dispensers with which the cartridge of the present invention is particularly adapted for use. An example of a new and improved piston-like dispenser is the subject of my co-pending U.S. application Ser. No. 07/801,243 which is incorporated herein by reference.

Most people encounter difficulty in applying drops to their eyes. The eye is a very sensitive body part and individuals find it difficult to control reflexive blinking when applying drops thereto. Also, eye drop users often have poor vision. Poor vision makes it difficult to position the tip of the dropper bottle over the eye and frequently causes drops to be incorrectly applied to the nose or cheek. Additionally, elderly people often have difficulty holding a dropper bottle steady or encounter difficulty in squeezing the bottle to apply a proper quantity of the medicament.

Even if the liquid medicament is properly applied to the eye, the medicament's effectiveness is limited. The minimum volume of a drop of liquid medicament which can ordinarily be introduced into contact with an eye at one time is about 30 μl. Any amount which is greater than about 25 μl usually spills over the eyelid onto the cheek since this is the maximum volume which the eye can ordinarily handle. When eye drops are applied to the surface of the eyeball, blinking and natural tear flow combine to limit the time to a few minutes that liquid medicament will remain effective.

On the other hand, if medicament is applied to the cul de sac of the conjunctiva, the medicament will remain effective for a longer period of time, maximizing the benefits of applying drops of liquid medicament to the eye. This is because the conjunctiva is an area of low sensitivity and low tear turnover such that blinking and tearing are avoided. However, because of the difficulty encountered in steadying the dropper and accurately positioning it over the conjunctiva, maximizing the effectiveness of the medicament remains elusive.

U.S. Pat. No. 4,543,096 describes and illustrates an apparatus having finger-like projections which are attached to the front of an eye drop bottle to spread the eyelids apart during the eye drop dispensing process. One moveable finger is connected to a lever for both depressing the lever and simultaneously causing the eyelids to spread apart while forcing a drop from the dropper bottle. However, the apparatus described in U.S. Pat. No. 4,543,096 cannot be used with the accordion-like or piston-like dispensers which are actuated by compression in the longitudinal direction rather than from the sides. Furthermore, this apparatus will not properly expose the cul de sac.

Similarly, U.S. Pat. No. 4,531,944 depicts an apparatus for steadying the tip of a dropper over the eye and further includes a sighting hole to distract the eye. However, this apparatus does not have a means to expose the cul de sac nor keep the lower eyelid depressed.

Typical eye-drop dispensers also have the disadvantage that the force which is necessary to actuate the dispenser to emit a drop is not in the same direction as the motion which is necessary to lower the lower eyelid and expose the cul de sac. It would be desirable to have a device which actuates the dispenser with a motion which is in the same direction as that which is necessary to lower the lower eyelid.

SUMMARY OF THE INVENTION

It is an object of the invention to provide a device which can accurately deliver a small drop of medicament to the conjunctival cul de sac of an eye.

It is a further object of the invention to provide such a device which can be used to actuate an accordion-like or piston-like vial-dispenser using minimal force.

It is a further object of the invention to provide such a device wherein the motion used to actuate the dispenser to emit a drop is in the same direction as the motion which is necessary to depress the lower eyelid and expose the conjunctival cul de sac.

It is a further object of the invention to provide a device having these features which has a simple construction and which is easy to manufacture.

The foregoing objects are achieved by the present invention which provides a cartridge which is particularly adapted for actuating an accordion-like or piston-like dispenser-vial. The cartridge includes a generally cylindrical housing which is adapted to receive a dispenser-vial between an anterior wall of the housing and a telescoping cylinder. The anterior wall of the housing has an aperture for allowing the nozzle of the vial to project therefrom. The anterior of the housing is curved with a highly polished and smooth external surface to prevent any corneal injury in the event of accidental contact with the eye.

The back of the housing is open and slidably receives the telescoping inner cylinder. When the inner cylinder is pushed toward the anterior of the housing it forces the dispenser-vial to compress in the longitudinal direction between the anterior wall of the housing and the cylinder. In the case of some dispensers which can be used with the invention, compression causes a drop of liquid medicament to enter the drop cavity of the dispenser thereby "loading" the drop cavity.

The top of the inner surface of the housing is formed with a notch. The front of the telescoping inner cylinder is formed with a rearwardly and outwardly projecting extension which easily slides past an inclined side of the notch as the cylinder is pushed into the housing to load the drop cavity of the vial. However, the opposite side of the notch is angled to prevent the cylinder extension from sliding past the notch in the opposite direction, thereby locking the cylinder so that the vial is in its loaded position.

The housing is formed with a trigger mechanism for unlocking the cylinder. A trigger button is disposed on the top of the housing. Depression of the trigger button forces the extension of the inner cylinder away from the notch allowing the cylinder to move past it. The compressed dispenser-vial forces the inner cylinder rearward. Upon expansion of the dispenser-vial a drop is emitted through the dispenser nozzle.

The bottom of the anterior section of the housing is formed with a soft finger which is adapted to engage the lower eyelid. In order to apply a drop, the inner cylinder is pushed into its locked position to load the dispenser-vial. The nozzle projecting from the cartridge is then positioned over the eyeball with the finger pressing on the lower eyelid to expose the conjunctival cul de sac. When the trigger is depressed the resulting motion of the cartridge will be in the sam direction as the motion which causes the finger to lower the lower eyelid and expose the conjunctival cul de sac as a drop is emitted.

DETAILED DESCRIPTION OF THE INVENTION

Figure 1:
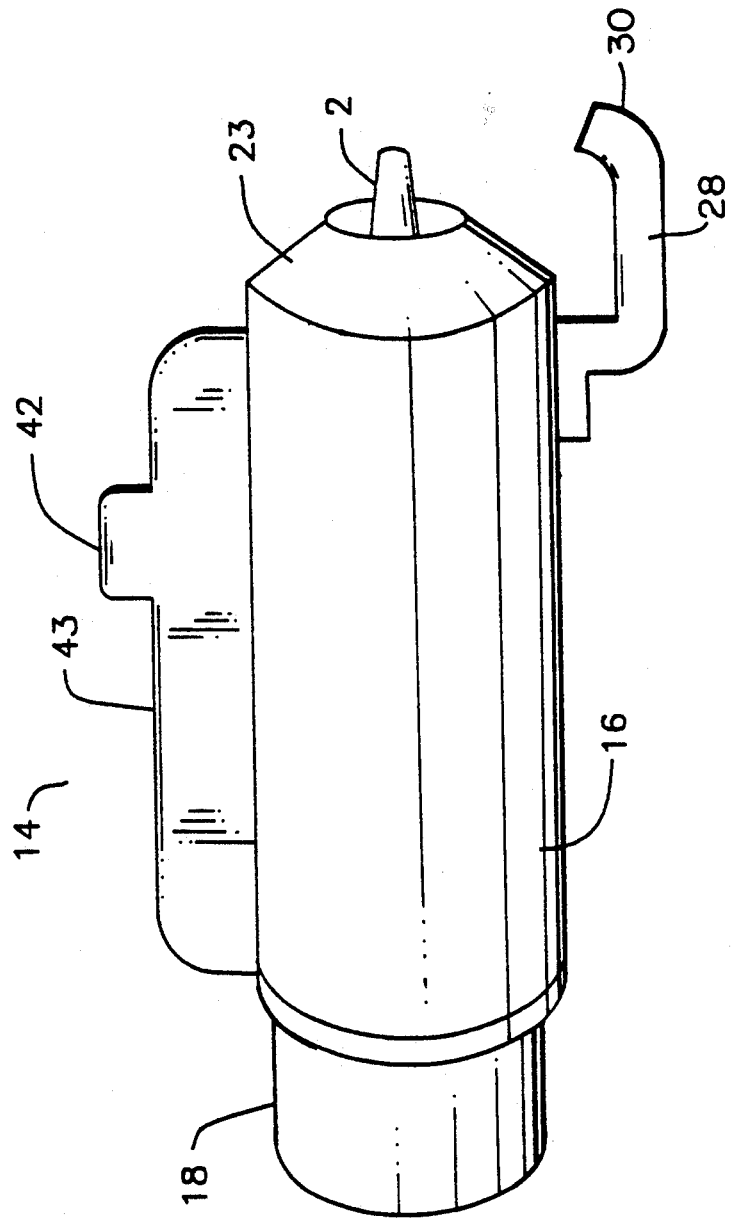
FIG. 1 is a perspective view of a cartridge in accordance with the invention.

The cartridge of the invention is specially adapted to work in conjunction with an accordion-like or piston-like dispenser-vial. An example of a new and improved piston-like dispenser which can be used in the cartridge of the invention is the subject of my co-pending application Ser. No. 07/801,243 which is incorporated herein by reference, however, the present invention is not limited to use with this particular dispenser. Parts of a dispenser described in application Ser. No. 07/801,243 which are relevant to an understanding of the present invention are illustrated in FIG. 2 and will now be described briefly to facilitate understanding of the cartridge.

The dispenser-vial includes a nozzle 2, wings 3, a bellows portion 4, wings 6 and a rear vial section 8 containing a storage supply of liquid medicament. The dispenser is compressible in the longitudinal direction between its posterior wall 10 and the anterior nozzle 2. For this purpose, the bellows portion 4 is constructed of a soft flexible plastic material such as the thermoplastic resin sold under the name Kraton from the Shell Company. Resiliency of the dispenser can be provided by the spring quality of the accordion bellows made of Kraton. Kraton has an excellent memory and can be an excellent spring. Alternatively, resiliency may also be provided by a longitudinally disposed spring (not illustrated) which urges the dispenser to expand upon compression.

Figure 4:
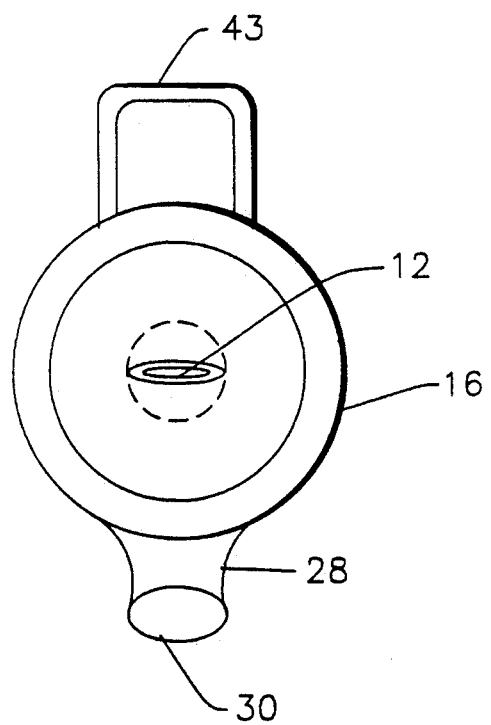
FIG. 4 is a view of the cartridge from the anterior.

The dispenser includes a drop cavity therein (not illustrated) which holds a predetermined volume of fluid to be emitted in the form of a drop. Compression of the dispenser in its longitudinal direction creates a drop in pressure in the drop cavity to fill or "load" the drop cavity with liquid where it is stored until it is emitted as a drop from the slit 12 (see FIG. 4) in nozzle 2. This compressed state will be referred to herein as the loaded state. Expansion of the dispenser from the loaded state (caused by the spring urges the fluid in the drop cavity under pressure toward the nozzle 2 from which it is emitted in the form of a drop. It can be seen that the force which is required to actuate this type of dispenser must ordinarily be applied in the direction of the nozzle and hence the eye. With this background information about the operation of the piston-like dispenser in mind, the cartridge of the invention will now be described.

Figure 2:
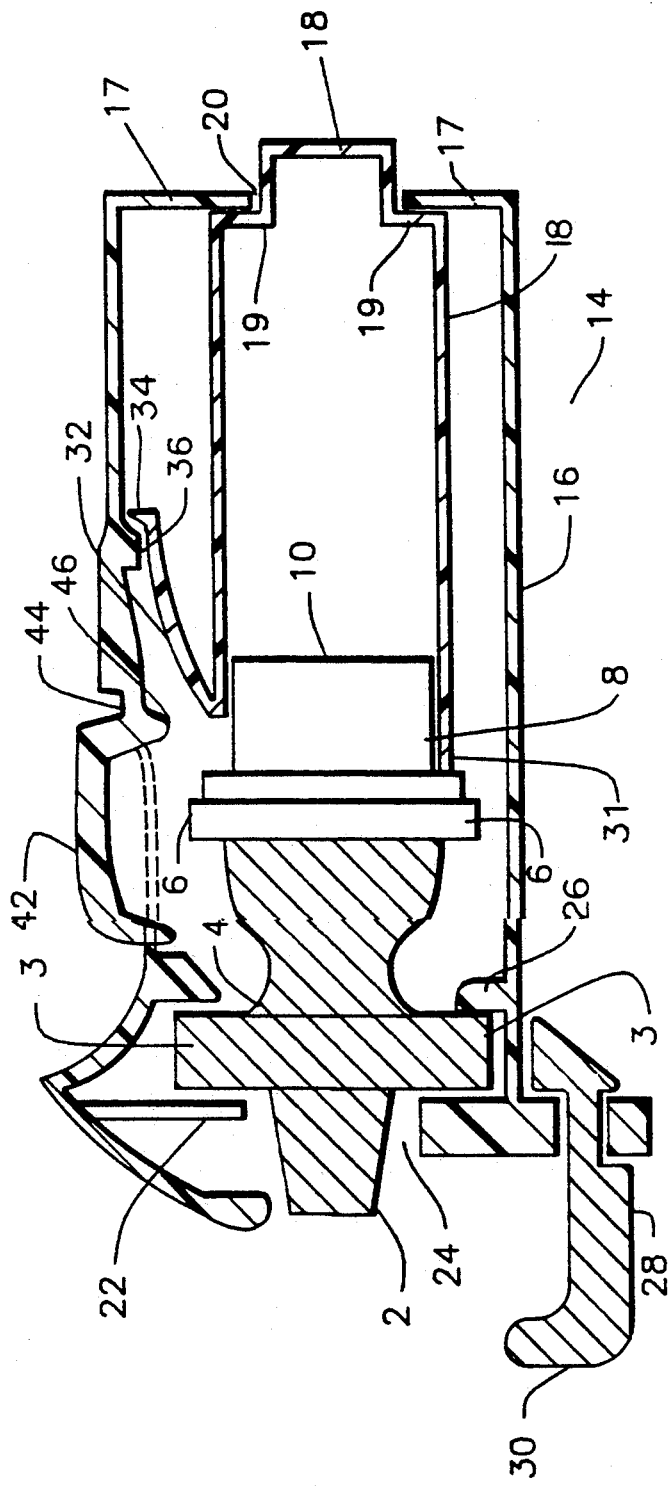
FIG. 2 is a detailed cross-sectional side view of a cartridge in accordance with the invention containing a dispenser-vial.

Referring to FIGS. 1 and 2, the cartridge which is generally indicated at 14 includes a cylindrical housing 16 which slidably receives an inner cylindrical member 18 through a back open end 20. Preferably, the back of the housing 16 has a wall 17 to fit around the portion of the cylinder 18 which projects outside of the housing. The wall 17 will abut a recessed portion 19 of the inner cylinder 18 to close off the housing to external vapor and moisture.

The front of the housing 1 is substantially closed by an anterior wall 22 which has an aperture 24 centrally located therein allowing for the projection of the nozzle 2 of the dispenser. Preferably, the front of the housing 16 has a smooth arcuate external surface 23 (see FIG. 1) in the event that the cartridge accidentally makes contact with the face. When the dispenser is mounted in the cartridge it sits between the anterior wall 22 and the member 18 as illustrated. The inner surface of housing 16 includes an annular rim 26. Anterior wall 22 and annular rim 26 wedge wing 3 of the dispenser therebetween to prevent displacement of the dispenser within housing 14.

The lower anterior section of housing 16 includes a forwardly projecting finger 28 which extends from the housing 16 beyond the tip of nozzle 2. The finger is upwardly curved to define a smooth surface 30 for engaging the lower eyelid. The finger is preferably coated with a material such as Kraton.

The inner cylinder 18 has a front section 31 which is attached to the vial section 8 of the dispenser. If desired, the inner cylinder 18 may be formed integrally with the storage section 8. The front upper section of the inner cylinder 18 has an outwardly and rearwardly projecting extension 32 which engages and presses against the inner surface of housing 16. The extension 32 is flexible in the direction transverse to the longitudinal axis of the cartridge 14. The tip 34 of the extension 32 has a surface which is positioned and adapted to engage a notch 36 formed on the inside surface of housing 16. The notch 36 is inclined and smooth on its posterior side 38 but is cornered with the housing wall on its anterior side 40. The inner cylinder 18 and extension 32 are positioned in the housing such that the tip 34 of the extension is posterior to the notch 36 when the dispenser is in the non-loaded position.

The cartridge 14 includes a trigger 42. The trigger 42 may be slidably positioned in an opening of an upper housing 43 (see FIG. 1) so as to be capable of inward movement toward the central longitudinal axis of the cartridge. Alternatively, the trigger 42 may be integrally formed with the housing 16 so that it pivots about a thin-walled living hinge section 44 (see FIG. 2). The inner surface of the trigger is formed with a projecting heel 46 whose function will become apparent from the following description of the operation of the cartridge. As illustrated in FIG. 2, preferably the trigger 42 and the point of attachment of the finger 28 to the housing 16 are disposed on opposite upper and lower sides of the housing, respectively, so that they are disposed along the housing 180° apart.

Before positioning the cartridge 14 over the eye, the dispenser-vial in the cartridge is first loaded by pushing the inner cylinder 18 inward thereby compressing the bellows 4 of the dispenser. As the inner cylinder 18 is pushed inward the extension 32 is forced to flex as it slides over notch 36. The tip 34 of extension 32 is able to smoothly slide over the inclined surface 38 of notch 36. Once the tip 34 has passed over the notch 36 the extension 32 will snap back into engagement with the inner surface of housing 16. At this point the dispenser will be in its loaded state as previously defined. In addition, the cartridge 14 is in a locked position because the tip 34 of extension 32 will be unable to move over the cornered surface 40 of notch 36. The cartridge 14 is now ready for positioning over the eye.

As discussed above, a drop of medicament is ideally deposited in the conjunctival cul de sac of the lower eyelid for maximum effectiveness. For this purpose, the engaging surface 30 of finger 28 is gently pressed on the lower eyelid. The cartridge is then moved downward slightly to expose the cul de sac and the cartridge is positioned so that the nozzle 2 will be directed toward the cul de sac. At this point the user would depress the trigger 42.

Figure 3:
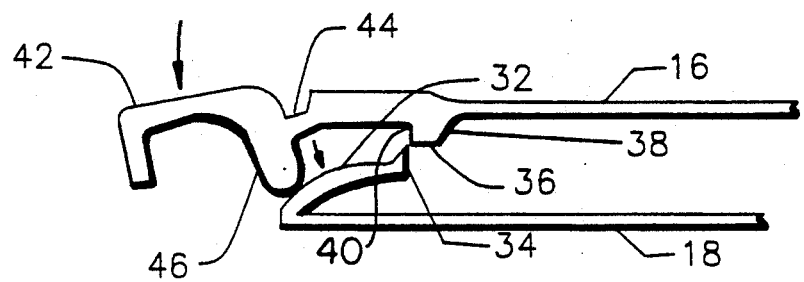
FIG. 3 is an isolated detailed view of the trigger mechanism of the cartridge of the invention.

Referring to FIG. 3, when the trigger 42 is depressed the heel 46 will force the extension 32 downward and the tip 34 will eventually clear the face 40 of notch 36. The spring in the dispenser will force the dispenser and the inner cylinder 18 to expand back to the non-loaded position and at this time a drop of medicament will be released from the slit 12 of nozzle 2 into the eye as discussed above.

It should be appreciated that one advantage of the cartridge of the invention is that the motion which is used to depress the trigger and thereby release a drop is in the same direction as the motion used to lower the eyelid and expose the cul de sac. Therefore, more accurate delivery of the drop is possible. Furthermore, an area of low sensitivity and low tear turn over is specifically targeted by the cartridge which prevents tearing and blinking reflex for better efficacy.

In addition, there is no danger of poking the eyeball with the nozzle 2 since the motion to depress the trigger is not in the direction of the eye and since the finger 28 extends beyond the nozzle. Moreover, when the trigger is depressed the return mechanism of the vial projects the inner cylinder in the direction away from the eye. The cartridge is particularly useful for arthritic patients because the trigger mechanism allows for easy release of a drop.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A cartridge for use with a dispenser for applying medicament to an eye comprising:
    a housing having an anterior wall with an aperture therein, the housing having an open back end;
    a longitudinally slidable member contained within, said member having a flexible outwardly projecting extension which has a tip engaging an inner surface of the housing;
    a notch disposed on the inner surface of the housing having an anterior face and a posterior face which are angled to the housing and which cooperate with the extension tip such that the extension tip can be forced over the posterior face upon sliding the slidable member toward the anterior wall to a locked position where the tip engages the anterior face of the notch, but the tip cannot be forced over the anterior face upon sliding the member toward the back end of the housing from the locked position; and
    a trigger in the housing having an inner surface for engaging the flexible extension, said trigger being movable to a position where its inner surface forces the flexible extension tip in its locked position in a direction towards the slidable member and away from the inner surface of the housing so that the tip is free to move past the notch upon sliding of the slidable member away from the anterior wall.

2. The cartridge according to claim 1 wherein the housing is cylindrical and wherein the finger is attached along the housing at a point which is about 180° from the location of the trigger.

3. The cartridge according to claim 1 wherein the finger has a surface of a soft thermoplastic material.

4. The cartridge according to claim 1 wherein the inner surface of the trigger has a projecting heel for engaging the flexible extension tip.

5. The cartridge according to claim 1 wherein the posterior face of the notch is a smooth inclined surface and wherein the anterior face of the notch is a flat surface which is normal to the inner surface of the housing.

6. The cartridge according to claim 1 further comprising a finger for engaging an eyelid, the finger projecting from an outer surface of the housing and extending out to a point anterior to the anterior wall.

7. A cartridge in combination with a dispenser for applying medicament to an eye, the dispenser being of the type which is actuated to load a drop of medicament into a cavity therein by compression in its longitudinal direction to a compressed position and which is actuated to emit said drop from a nozzle upon subsequent expansion from said compressed position, the cartridge comprising:
    a housing retaining the dispenser therein, the housing having an anterior wall with an aperture therein receiving the nozzle of the dispenser and the housing having an open back end;
    a telescoping member, contained within for compressing the dispenser in its longitudinal direction;
    a means for locking the telescoping member in a position where the dispenser is in a compressed position; and
    a trigger means for disengaging the means for locking to allow the dispenser to expand from said compressed position.

8. The cartridge according to claim 7 further comprising a finger for engaging an eyelid, the finger projecting from the housing in an anterior direction to a point anterior to the anterior wall.

* * * * *